United States Patent [19]
Siegfried et al.

[11] Patent Number: 5,989,527
[45] Date of Patent: Nov. 23, 1999

[54] COMPOSITIONS AND METHODS FOR IMPROVING THE PERFORMANCE OF CHEMICAL EXFOLIATING AGENTS, SUNLESS TANNING AGENTS, SKIN LIGHTENING AGENTS AND INSECT REPELLENTS

[75] Inventors: Robert W. Siegfried, Medford; Rocco Burgo, Cherry Hill, both of N.J.; Andrew P. O'Connor, Drexel Hill, Pa.; Diana L. Smith, Tabernacle, N.J.

[73] Assignee: Inolex Investment Corporation, Wilmington, Del.

[21] Appl. No.: 09/012,995

[22] Filed: Jan. 26, 1998

[51] Int. Cl.⁶ .......................... A61K 7/42; A61K 47/34; A01N 25/10
[52] U.S. Cl. .............................................. 424/59; 424/409
[58] Field of Search .................................. 424/59, 60, 409

[56] References Cited

U.S. PATENT DOCUMENTS

| | | | |
|---|---|---|---|
| Re. 29,871 | 12/1978 | Papantonioo et al. ........... | 424/59 |
| 3,873,725 | 3/1975 | Skinner et al. . | |
| 3,895,104 | 7/1975 | Karg ................................. | 424/60 |
| 3,980,617 | 9/1976 | Jaquet et al. ..................... | 424/59 |
| 5,000,945 | 3/1991 | Kobayashi et al. . | |
| 5,041,281 | 8/1991 | Strobridge ....................... | 424/60 |
| 5,154,855 | 10/1992 | Sekiguchi et al. . | |
| 5,158,762 | 10/1992 | Pierce . | |
| 5,160,738 | 11/1992 | Macaulay et al. . | |
| 5,223,559 | 6/1993 | Arraudeau et al. . | |
| 5,224,665 | 7/1993 | Natraj et al. . | |
| 5,229,105 | 7/1993 | Wilmsmann . | |
| 5,302,377 | 4/1994 | Pereira et al. . | |
| 5,385,730 | 1/1995 | Ichinohe . | |
| 5,411,729 | 5/1995 | O'Lenick, Jr. . | |
| 5,411,734 | 5/1995 | Vargas et al. . | |
| 5,411,802 | 5/1995 | Kumar et al. . | |
| 5,439,682 | 8/1995 | Wivell et al. . | |
| 5,616,598 | 4/1997 | Lion et al. . | |
| 5,624,676 | 4/1997 | Mackey et al. . | |
| 5,653,965 | 8/1997 | Narayanan et al. ............. | 424/59 |

FOREIGN PATENT DOCUMENTS

| | | |
|---|---|---|
| 0 506 961 A1 | 10/1992 | European Pat. Off. . |
| 62-079258 | 4/1987 | Japan . |
| 1412789 A1 | 7/1988 | Russian Federation . |
| 1421344 A1 | 9/1988 | Russian Federation . |
| WO 96/06878 | 3/1996 | WIPO . |
| WO9606878 | 3/1996 | WIPO . |
| WO 97/49380 | 12/1997 | WIPO . |

OTHER PUBLICATIONS

W.G. Reifenrath et al., "Evaporation and Skin Penetration Characteristics of Mosquito Repellent Formulations," *Journal of the American Mosquito Control Association*, vol. 5, No. 1 (Mar. 1989), pp. 45–51.

Inolex Chemical Company, *An Introduction to LEXOREZ® 100*—compilation of evaluative data and the like. Some pages dated 1994 and others 1995, total pages 48.

*Primary Examiner*—Peter F. Kulkosky
*Attorney, Agent, or Firm*—Panitch Schwarze Jacobs & Nadel P.C.

[57] ABSTRACT

Topical compositions for application to the stratum corneum include a polyester and an active ingredient which is a chemical exfoliating agent, sunless tanning agent, skin lightening agent and/or an insect repellent. The polyester substantially retains the active ingredient on or in the stratum corneum. A method for improving the effect of the active ingredient in a topical composition includes providing a polyester which functions to substantially retain the active ingredient on or in the stratum corneum to improve the effect of the active ingredient.

32 Claims, No Drawings

COMPOSITIONS AND METHODS FOR IMPROVING THE PERFORMANCE OF CHEMICAL EXFOLIATING AGENTS, SUNLESS TANNING AGENTS, SKIN LIGHTENING AGENTS AND INSECT REPELLENTS

BACKGROUND OF THE INVENTION

The use of chemical exfoliating agents such as alpha- and beta-hydroxy acids is associated with fresher, smoother-looking skin. The main function of these acids is to exfoliate the skin by weakening the bonds that hold the cells together in the skin's upper most layers, i.e., the stratum corneum. The overall effect is described as combating wrinkles, photoaging, and loss of smoothness and elasticity. The basis for the significant impact of alpha- and beta-hydroxy acids as skin treatments is their ability to reduce corneocyte adhesion and to accelerate cell proliferation within the basal layer of the stratum corneum. Continued use of these ingredients in topically applied compositions provides a gradual reduction in fine lines and an improvement in skin texture by virtue of accelerated desquamation.

Alpha-hydroxy acid compositions of the prior art may include fatty acid glycols, and surfactants and emulsifiers which may be silicon polymers, or humectants which may include functionalized silicone polymers. U.S. Pat. No. 5,000,945 combines organic acids with oils and sunscreens in fatty acid-based compositions which may have glycol surfactants. U.S. Pat. No. 5,244,665 includes citric acid triester monomeric compounds, polyethylene emulsifiers, and silicone emulsifier/surfactants. U.S. Pat. No. 5,439,682 is directed to a skin cleansing moisturizing composition including functionalized silicone polymers, as a dispersed insoluble oil phase, and hydroxy acid humectants.

Skin-care products which act against aging effects or which remove or lessen age-induced wrinkles are of increasing demand to consumers. Topically applied compositions having alpha- and beta-hydroxy acids such as lactic or glycol acids exhibit improved effects in relation to prior active ingredients asserted to reduce aging over a prolonged period of use. However, consumers may experience dissatisfaction if the desired effects are not readily perceived, or if they experience the undesirable side effects of topical compositions which may cause a stinging sensation as a result of the presence of the acids in the composition. Based on these difficulties, consumers may stop using the products altogether, or, in the case of stinging or burning sensations, may deter other potential users from trying the products. These problems may also lead to intermittent usage of such skin care products which then compromises the ultimate beneficial effects of long-term usage.

As such, there is a need in the art for a composition which enhances the performance of skin exfoliating agents such as hydroxy acids and which minimizes skin irritancy typically associated with their use.

In addition to attempts to reduce the effects of skin aging caused by natural aging processes, there is increased interest in protecting skin from the effects of the sun. With the ever-increasing rate of damage to the skin associated with exposure to UV radiation, including the risk of melanoma, consumers are looking for ways to guard the skin from sun exposure, such as by using various sunscreen-containing topically applied compositions. However, many consumers still seek to achieve the look of a tan or a "healthy" coloring to their skin without incurring the risks involved with actually tanning by harmful exposure to the sun's radiation.

One way of achieving this affect cosmetically is to use compositions containing "sunless tanning" active ingredients. While sunless-tanning agents have been used for many years, they have not provided adequate tanning effects with respect to color, substantivity and harmlessness to the skin. The tanning mechanism consists of a Maillard reaction of dihydroxyacetone (DHA) with amines of the stratum corneum to yield brown polymeric structures on the skin. The molecule reacts with the skin in as short a time as three hours, providing a brown color which typically lasts for only up to a few days. Cosmetics manufacturers, as well as consumers of such products, desire a product which would enhance the color development and prolong the developed color.

While modern cosmetic products attempt to reduce the effects of aging and avoid exposure to the sun while providing enhanced coloring, as noted above, there is also a desire of many consumers to alter their existing skin appearance with respect to the effects of hyperpigmentation. Such effects may include dark patches, freckles or other skin pigmentation effects. Topically applied compositions are available to make skin appear lighter or to retard or inhibit pigmentation. Lightening may be achieved by applying pigmentation to the skin surface, by reducing the normal pigmentation process which continuously occurs, or by bleaching extracellular and relatively fixed pigment. Products associated with applying pigmentation to the skin surface, such as cosmetics, must be present on the skin surface continuously to achieve the effect of a lighter complexion. Cosmetics containing active ingredients which are designed to reduce the normal pigmentation process or which bleach extracellular pigment can be applied at definite intervals over a period of time. The overall effects of depigmentation are achieved by the mechanisms of either reducing pigmentation by decolorizing the melanin already present in the skin and/or by preventing new melanin from being formed. Products which can accelerate and improve these mechanisms are desired in the cosmetics industry.

In addition to the above cosmetic products which are in increasing demand, there is a need in the art for protective topical compositions which provide insect repellent capabilities for prolonged periods of time without causing detrimental harm to the user from penetration of the repellent. The increased incidence of mosquito- or other insect-borne health problems, such as encephalitis has heightened the public demand for such products. The most popular such repellent, which has been in use for many years, is N,N-dimethyl-m-toluamide (DEET). In order for DEET to be effective, however, it must remain on or in the outermost layers of human skin. Absorption of DEET through or deep into the epidermis of the user may sensitize the user to DEET's effect and render the use of the repellent incapable of performing its function. As such there is a need in the art to localize DEET in the outer stratum corneum or on top of the skin to enhance its effectiveness and to avoid sensitizing users to DEET's harmful side effects.

Applicants previously investigated the effects of various end-functionalized polyesters in general for use in hair and skin personal care products. The results of this investigation and early experimentation are set forth in WO 96/06878, the entire teaching of which is incorporated herein by reference. Such derivatized polyesters appeared promising in a number of areas, spurring further research and development using the variety of such polyesters as well as other polyesters. As a result of further research, applicants have found as described herein that certain polyesters, functionalized polyesters, and their derivatives, when used with particular active ingredients can significantly and unexpectedly enhance the performance of such active ingredients.

U.S. Pat. No. 5,160,738 teaches a cosmetic composition which uses particular polyol fatty acid polyesters as an alternative to petrolatum for skin and hair products as occlusive agents. The compositions include a blend of two or more polyol fatty acid polyesters derived from aliphatic or aromatic polyols of at least 4 free hydroxyl groups, at least 60% of which are esterified with one or more fatty acids of from 8–22 carbon atoms.

U.S. Pat. No. 5,411,729 discloses polyester humectants for hair and skin for lubricating, softening and conditioning. The humectants are derived from esterification of hydroxyl-containing silicone compounds, diacid and polyhydroxy compounds.

Based on the foregoing, there is a need in the art for improved topical compositions with chemical exfoliating agents having decreased irritation and which provide improved and/or better controlled effects of such agents in cell renewal and desquamation. There is also a need for a composition which can maintain sunless tanning agents on the surface of the skin for a prolonged period, assist in color development and maintain a persistent color from use of these agents. There is further a need in the art for a composition having skin lightening agents and/or insect repellents such as DEET which can maintain these compositions on the surface of the skin and significantly enhance their effectiveness.

BRIEF SUMMARY OF THE INVENTION

The invention includes a topical composition for application to the stratum corneum, which comprises a polyester and an active ingredient selected from the group consisting of a chemical exfoliating agent, a sunless tanning agent, a skin lightening agent, and an insect repellent. The polyester functions to substantially retain the active ingredient on or in the stratum corneum.

In one embodiment, the invention includes a topical composition for application to the stratum corneum which comprises a polyester having a backbone derived from the reaction of at least one linear or branched diol and at least one linear or branched diacid. The polyester has a molecular weight of from about 500 to about 100,000. The composition also comprises an active ingredient selected from the group consisting of a chemical exfoliating agent, a sunless tanning agent, a skin lightening agent and an insect repellant. The polyester functions to substantially retain the active ingredient on or in the stratum corneum.

The invention further includes a method for improving an effect of an active ingredient in a topical composition, comprising providing to said topical composition a polyester, wherein the active ingredient is selected from the group consisting of a chemical exfoliating agent, a sunless tanning agent, a skin lightening agent, and an insect repellent and the polyester functions to substantially retain the active ingredient on or in the stratum corneum to improve an effect of the active ingredient.

DETAILED DESCRIPTION OF THE INVENTION

The present invention provides improved topically administered compositions. Many topical compositions, when applied to the outer layers of the skin can wear off or penetrate to lower, deeper layers of the skin, and possibly the systemic circulation. When this occurs, the active ingredients have reduced effect and the potential for sensitization and irritation occurs. The following is a detailed description of the preferred embodiments of the present invention and is not intended to limit the scope of the invention.

During investigation of certain polyesters for general use in hair and skin formulations, applicants have discovered that certain polyesters, functionalized polyesters and their derivatives create unexpectedly improved effects when combined with particular active ingredients, specifically, chemical exfoliating agents, sunless tanning agents, skin lightening agents and insect repellents. While the polyesters and active ingredients may be referred to in this detailed description in the singular form, it will be understood, based on this disclosure, that more than one polyester and/or various combinations of the preferred active ingredients may be used in compositions within the scope of the invention.

The polyesters suitable for use in the compositions are those which include a backbone derived from the reaction of at least one diol and at least one diacid. The diol is preferably a linear or branched aliphatic dihydric compound having two —OH groups. The diacid is preferably a linear or branched chain aliphatic dicarboxylic acid having two —COOH groups, although aromatic acids may also be used. The polyester backbone is preferably derived from the co-condensation of such diols and diacids. The diol may contain from 2 to 10 ether linkages (—R—O—R—) or from 2 to 10 tertiary amine groups ($NR_3$). The polyester may be linear or cross-linked as described below.

While the resulting polyesters generally contain —OH and/or —COOH functionality, they may be —OH end-functionalized, or preferably, the polyester is further functionalized and/or cross-linked by reacting the at least one diol and at least one diacid as noted above with at least one polyfunctional acid or polyfunctional alcohol, preferably having a functionality of at least 3 with respect to the —OH or —COOH groups. While use of bifunctional reactants may produce polyesters having functionalities of less than 2, preferably, the polyfunctional acid or polyfunctional alcohol should be provided in an amount sufficient to provide a polyester which has an enhanced functionality, either —OH or —COOH, of at least 2 and a molecular weight of preferably from 500 to 100,000. While the use of a polyfunctional acid or polyfunctional alcohol is preferred for increasing the functionality of the polyester, other suitable methods may be used provided the resulting polyester has an acceptable molecular weight and achieves an equivalent level of functionality. Preferably, if a polyfunctional acid or polyfunctional alcohol is used, it is provided in an amount of up to about 50 percent by weight of the other reactants. The resulting polyesters are either hydroxy or acid functional and preferably have either —OH or —COOH terminal end groups which thereby provides a functionalized polyester having a functionality of at least 2. A greater degree of functionality, in terms of functional groups per unit mass, is obtained if the molecular weight of the polyester is lower. Crosslinking provides an increase in crosslink density as well as contributes to increasing functionality.

The amount of acid or alcohol to be used, in equivalent weight, is determined in accordance with the number of —OH or —COOH groups, or equivalents, to be provided per unit mass of polymer. The molecular weight of the acid or alcohol can then be used to calculate the appropriate weight percentage of acid or alcohol required to achieve the desired number of equivalents. Preferably, one or less equivalent of acid or alcohol is provided per equivalent desired in the final polymer such that the resulting polymer will have substantially no free acid or alcohol remaining and all of the acid or alcohol will be used in the functionalizing reaction. As such, the equivalents and moles of acid and alcohol are selected to provide the desired molecular weight for the polyester and the desired hydroxyl and/or acid content per unit mass in the polyester.

The diacids used for forming the polyesters are preferably of from 2 to 20 carbon atoms. Suitable aliphatic diacids for use in forming the polyesters include, for example, malonic acid, maleic acid, fumaric acid, acetylene dicarboxylic acid, succinic acid, glutaric acid, adipic acid, pentanedioic acid, muconic acid, pimelic acid, suberic acid, azelaic acid, sebacic acid, undecandioic acid, traumatic acid and branched and linear alkyl, alkenyl and nonaromatic cycloalkyl and nonaromatic cycloalkenyl derivatives of those acids. Preferably, the acid is adipic acid or a branched alkyl derivative of an aliphatic acid. Preferred linear aliphatic diacids are adipic acid, glutaric acid, succinic acid, azelaic acid, and sebacic acid. Preferred branched diacids are hydrogenated and unhydrogenated dimer acids. Cyclic aliphatic acids are also useful with a preferred cyclic acid being cyclohexanedicarboxylic acid. Aromatic acids may also be used, such as orthophthalic acid, isophthalic acid and terephthalic acid. One skilled in the art, based on this disclosure, would be aware that such a list of possible diacids is exemplary in nature and that other suitable diacids having similar properties are within the scope of this disclosure.

Suitable diols for use in forming the polyesters include any alkane diol, alkene diol, alkyne diol, nonaromatic cycloalkane diol or nonaromatic cycloalkene diol and their derivatives. Preferably, such diols have from 2 to 20 carbon atoms. Such diols include, for example, ethylene glycol, propylene glycol, 1,2 butanediol, 1,5-pentanediol, cyclopentanediol, 3,3-dimethyl-1,2-butanediol, 3-hexyne-2, 5-diol and the like. These diols are exemplary in nature and it should be understood by one skilled in the art, based on this disclosure, that the position of the —OH group on such diols may be varied. For example, 1,2 pentanediol, 1,3 pentanediol and 1,5 pentanediol are all suitable diols. Further, ether-containing diols having the formula HO—(CH$_2$—CH$_2$—O—)$_b$—CH$_2$—CH$_2$—OH, where b is from 1 to 5, may also be used. An example of a preferred ether group-containing diol for forming the polyester of the present invention is diethylene glycol. Examples of preferred branched chain diols for use in the invention include neopentyl diol, trimethylpentane diol and similar diols.

The above diacids and diols may be used singly or in a mixture of diacids and diols. Further, as noted above, when forming the polyesters of the present invention, a polyfunctional acid or polyfunctional alcohol may be added for crosslinking the polyester and/or providing an enhanced level of —OH or —COOH functionality. Suitable polyfunctional acids include any polycarboxylic acid having the preferred functionality as noted above. Suitable polyfunctional alcohols include functionalized alcohols having the required —OH functionality as noted above.

Preferably, a polyfunctional alcohol is used to provide crosslinking and/or additional —OH functionality to the polyester. Examples of suitable polyfunctional alcohols include 1,2,3-propanetriol (glycerin), 1,2,4-butanetriol, 1,1,1,-tris(hydroxymethyl)ethane, 1,2,6-trihydroxyhexane and the like. It will be understood from this disclosure that other polyfunctional alcohols or acids may be used to provide the required functionality and the above examples are not intended to be limiting.

The polyesters may be formed according to any suitable polymerization method. Preferably, the polyesters are formed by co-condensation of the diacids and diols in the presence of the functionalizing and/or crosslinking polyfunctional acid or polyfunctional alcohol.

In forming suitable polyesters for use in the present invention, the terminal end groups can be left as is and used in preferred topical compositions according to the present invention, or further end-functionalized by reacting with at least one compound, such as, for example, a linear or branched aliphatic monofunctional acid of from about 2 to 40 carbon atoms, a linear or branched monofunctional alcohol of from about 2 to 40 carbon atoms or combinations of such acids and alcohols. The polyesters can also be further end-functionalized by reacting them with primary or secondary amines or silicon-containing compounds. The amount of the functionalizing reactants provided are determined in accordance with the desired end-functionality. The number of equivalents per unit mass required to provide the specific functionality for a given application of the polyester is determined as described above. Based on the number of necessary equivalents per unit mass, the molecular weight of the functionalizing reactant is then used to determine the amount of that reactant to be provided to the reaction to achieve the specific functionality in the resulting polyester. Preferably, the equivalents are determined such that substantially no functionalizing reactant remains in a free form in the resulting polyester and substantially all of the reactant is used in the functionalizing reaction.

The linear and branched aliphatic monofunctional acids may include any carboxylic acid having from 2 to 40 carbon atoms. Examples of such acids include, formic acid, acetic acid, propionic acid, butyric acid, valeric acid, caproic acid, caprylic acid, capric acid, lauric acid, myristic acid, palmitic acid, stearic acid and similar linear aliphatic acids. The monofunctional group may be attached at any carbon site along the chain. Alkenyl, alkynyl, branched chain and non-aromatic cyclic acid derivatives of such linear acids having the appropriate monofunctionality may also be used, for example, 1-methylhexanoic acid or 4-hexenoic acid.

The linear and branched aliphatic monofunctional alcohols which may be used should be from about 2 to about 40 carbon atoms. Examples of such alcohols include methanol, ethanol, propanol, butanol, pentanol, hexanol and the like. The monofunctional hydroxyl group may be attached at any carbon site along the chain. Alkenyl, alkynyl, branched chain and nonaromatic cyclic alcohol derivatives of such linear alcohols having the appropriate monofunctionality may also be used, for example, propenol and similar alkenyl alcohols, isooctanol, 2-ethylhexanol, isodecanol, tridecanol and similar branched alcohols.

Exemplary cross-linked or linear polyesters for use in the present invention may be of Formula I below:

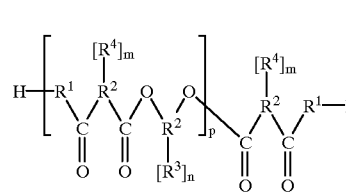

(I)

wherein: R$^1$ is independently either —O— or —O—R$^2$—O—;

R$^2$ is independently a linear or branched C$_2$–C$_{60}$ aliphatic group;

R$_3$ is —O—(C=O)—R$^1$—H, or —O—[(C=O)—R$_2$(R$^4$)$_m$—(C=O)—O—R$^2$(R$^3$)$_n$—O]$_p$(C=O)—R$^2$(R$^4$)$_m$—(C=O)—R$^1$—H;

R⁴ is —(C=O)—O—R¹—H, H, or —(C=O)—O—R²—O—[(C=O)—R²(R⁴)ₘ—(C=O)—O—R²(R³)ₙ—O]ₚ—(C=O)—R²(R⁴)ₘ—(C=O)—R¹—H;

m is independently an integer and $1 \leq m \leq 5$;

n is independently an integer and $1 \leq n \leq 5$; and p is independently an integer and $3 \leq p \leq 2000$.

Further examples of most preferred polyesters for use in the present invention include linear, acid-functional polyester polyols; hydroxy-functional polyester diols; linear, carboxylic acid-end-fucntionalized complex polyesters; linear, alcohol-end-functionalized complex polyesters; and the polyfunctional acid or polyfunctional alcohol cross-linked derivatives of these polyesters. Such preferred polyesters are shown below in Formulae II–IX:

Linear, Acid-Functional Polyester Polyol:

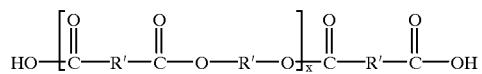
(II)

wherein R' is independently a linear or branched hydroxy-substituted or unsubstituted aliphatic $C_2$–$C_{60}$ group with from 0 to 200 ether linkages, a hydroxy-substituted or unsubstituted cyclic aliphatic $C_2$–$C_{12}$ group, or a hydroxy-substituted or unsubstituted aromatic group; and x is independently an integer and $3 \leq x \leq 2000$.

Acid-Functional Polyester Polyol Cross-linked With Polyfunctional Acid:

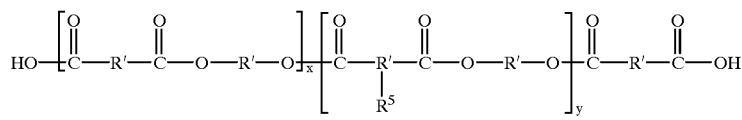
(III)

wherein R' and x are as defined above

R⁵ is —H, —(C=O)—OH or —[(C=O)—R'—(R⁵)_q—(C=O)—O—R'—O]_y—(C=O)—R'(R₅)_q—(C=O)—OH;

y is independently an integer and $3 \leq y \leq 2000$; and q is independently an integer and $0 \leq q \leq 5$.

Linear, Hydroxy-Functional Polyester Diol:

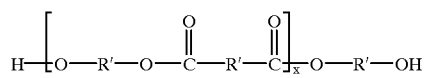
(IV)

wherein R' and x are as defined above.

Hydroxy-Functional Polyester Polyol Cross-linked With Polyfunctional Alcohol:

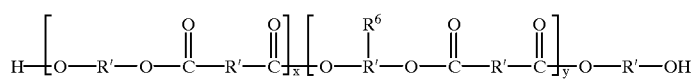
(V)

wherein x, y, q and R' are as defined above; and

R⁶ is —H, OH or —[O—R'(R₆)_q—O—(C=O)—R'—(C=O)]_y—O—R'(R⁶)_q—OH

Linear, Carboxylic Acid-End-Functionalized Complex Polyester:

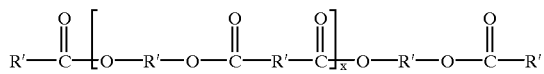
(VI)

wherein R' and x are as defined above.

Carboxylic Acid-End Functionalized Complex Polyester Cross-linked With Polyfunctional Acid:

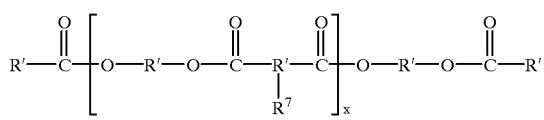
(VII)

wherein R', x and q are as defined above; and

R⁷ is H, —(C=O)—OH or —[O—R'—O—(C=O)—R'(R⁷)_q—(C=O)]_x—O—R'—O—(C=O)]_x—O—R'—O—(C=O)—R'(R⁷)_q

Linear, Alcohol-End-Functionalized Complex Polyester:

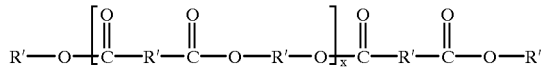
(VIII)

wherein R' and x are as defined above.

Alcohol-End-Functionalized Complex Polyester Cross-linked with Polyfunctional Alcohol:

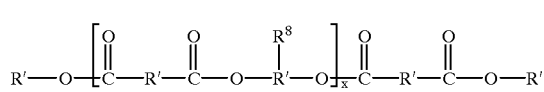

(IX)

wherein R' and x are as defined above; and

R$^8$ is H, —OH, or —[(C=O)—R'—(C=O)—O—R'(R$^8$)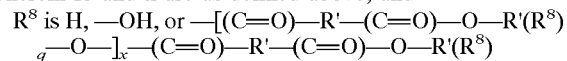

It should be understood based on this disclosure that while polyesters in accordance with the Formulae I-IX are preferred, other polyesters, such as those having mixed acid or alcohol-end functionalities or mixed polyfunctional alcohol and polyfunctional acid cross-linking may be used in the invention. In addition, any other suitable polyesters formed from co-condensation of compounds such as those described above which provide the desired effects for the specific active ingredients as noted herein may be used in the compositions of the present invention. Preferably, however, the preferred polyesters for use in the compositions according to the present invention have solubility parameters and molecular weights within a preferred range which will enable the polyester to function best in the topical compositions as described further below. Further, more than one polyester may be used in the compositions if the effect can be modified or otherwise enhanced to provide the ability to control the rate or degree of penetration of the active ingredient into the stratum corneum once the composition has been topically applied.

In addition to the foregoing, when using the monofunctional acids and alcohols to end-functionalize the polyesters, the monofunctional acids and alcohols may incorporate tertiary amine groups within the acid or alcohol chain.

Suitable primary and secondary amines which can be used for end-functionalizing the polyesters of the present invention include amines such as XNH$_2$ and X$_2$NH where the X group is a branched or linear nonaromatic alkyl, alkenyl or alkynyl chain of from 2 to 40 carbon atoms which may be further amine substituted. The reaction of such a primary or secondary amine with polyesters of the present invention produces an amine functionalized polyester, for example, having —NHX or —NX$_2$ end groups, where X is a described above in place of the —H or —R' on either end of the above Formulae. Exemplary primary and secondary amines include dimethylaminopropylamine, diethylaminoethylamine, aminoethylethanolamine, monoethanolamine, diethanolamine, isopropanolamine, commercially available saturated normal amines having from 6 to 24 carbon atoms and saturated secondary amines.

Exemplary silicon-containing compounds include polysilicones and/or polysiloxanes. Preferred polysiloxanes have an —Si(Y)$_2$O— repeating unit where Y is a lower alkyl group of from 1–4 carbon atoms. Hydroxy-terminal polysiloxanes and monomeric silicon-containing species may also be used in the present invention.

The polyesters of the compositions of the invention preferably are prepared such that they have a molecular weight within the preferred range of 500 to 100,000 and a solubility level which provides sufficient compatibility and co-solubility with the active ingredients as described further below as well as co-solubility with the wide range of general additives and base formulations for topically applied compositions. Preferably, the polyesters of the compositions of the invention have a Hildebrand solubility parameter which is from about 5 to about 25, and more preferably from about 5 to 12. Hansen-type or other solubility parameter theories may also be used as guidelines in determining a useful polyester from the preferred polyesters of the present invention. Using a polyester having a solubility level which is similar to both the active ingredients and the other components within a given cosmetic formulation minimizes separation of the formulation into phases. Solubility parameters, such as the Hildebrand parameters, may be easily found either in published information or readily discernible experimentally by any manner suitable in the art. In selecting a preferred polyester for a given composition according to the present invention, the solubility parameters of the active ingredient and other components in the topical formulation are preferably taken into account.

In order to select the appropriate polyester having the same or a similar solubility parameter, the factors to be taken into account are the ester density, degree of cross-linking and chain branching, the presence and quantity of functional groups and molecular weight. Because ester linkages are polar, in general, the higher the ester density, the greater the solubility parameter. Further mild crosslinking and chain branching will tend to increase intermolecular distance which will tend to disrupt the polyester's ability to interact favorably with other like molecules which would tend to lower the solubility parameter. If the polyester becomes highly cross-linked, the solubility behavior changes and is not easily predicted by solubility parameters, such that for these particular polyesters, the solubility will have to be experimentally determined. Use of or increase in number of functional groups will generally increase the solubility parameter for the polyester due to the polarity of most functional groups. Increases in molecular weight, in the absence of cross-linking, will typically reduce the solubility parameter at least to a point where additional chain length will have little effect. At very high molecular weight, the solubility parameters are less accurate such that predicting the solubility behavior will also have to be determined experimentally.

In addition to a polyester, or combination of polyesters, as described above, the topical composition of the present invention includes an active ingredient. The active ingredient is preferably at least one of a chemical exfoliating agent, sunless tanning agent, skin lightening agent, and insect repellent.

Chemical exfoliating agents which may be used in the claimed compositions include alpha- and beta-hydroxy acids, preferably of from 2 to 28 carbon atoms, as well as proteolytic enzymes, retinol or other similar compounds capable of causing desquamation of outer skin layers.

Examples of suitable alpha-hydroxy and beta-hydroxy acids include alkyl hydroxycarboxylic acids such as α-hydroxyethanoic acid (glycolic acid), α-hydroxypropanoic acid (lactic acid), 2-methyl-α-hydroxypropanoic acid (methyllactic acid), atrolactic acid, 2-hydroxy-1,2,3-propanetricarboxylic acid (citric acid), α-hydroxypropanoicbutanoic acid, α-hydroxy-isobutanoic acid, α-hydroxybutandioic acid (malic acid), dihydroxybutandioic acid (tartaric acid), α-hydroxypentanoic acid (α-hydroxyisovaleric acid) α-hydroxyhexanoic acid (α-hydroxycaproic acid), α-hydroxyisohexanoic acid (α-hydroxyisocaproic acid), 2,3,4,5-tetrahydroxyhexandioic acid (saccharic acid) α-hydroxyheptanoic acid, α-hydroxyoctanoic acid (α-hydroxycaprylic acid), α-hydroxynonanoic acid, α-hydroxydecanoic acid and similar acids; glucosemonocarboxylic acid (glucoheptonic acid), galacturonic acid, glucuronic acid, α-phenylhydroxyacetic acid (mandelic acid), tetrahydroxyadipic acid (mucic acid), pyruvic acid, β-phenyl-lactic acid, β-phenylpyruvic acid, 3-hydroxybutanoic acid (β-hydroxybutyric acid), tartronic acid, lactones such as glucoronolactone and gluconolactone, and esters and alkyl and alkenyl derivatives of these compounds. Proteolytic enzymes may also be used as chemical exfoliating agents, such as papain, pepsin, peptidase, trypsin, enterokinase. Additional examples of chemical exfoliating agents include retanoic acid and its derivatives.

Examples of phenyl-α-hydroxy acid derivatives which may be used in the compositions of the present invention include phenyl-α-acetoxyacetic acid, phenyl-α-acetoxypropanoic acid, phenyl-α-methyl-α-acetoxyacetic acid, phenyl-α-methyl-α-acetoxypropanoic acid, diphenyl-α-acetoxyacetic acid, dibenzyl-α-acetoxyacetic acid, phenyl-α-benzyl-α-acetoxyacetic acid, phenyl-α-benzoyloxyacetic acid, phenyl-α-methyl-α-benzoyloxyacetic acid, diphenyl-α-benzoylacetic acid, phenyl-α-phenylacetoxyacetic acid, phenyl-α-methyl-α-phenylacetoxyacetic acid, and diphenyl-α-phenylacetoxyacetic acid. Phenyl-α- or phenyl-β- acyloxyalkanoic acid derivatives may also be used in the present invention, such as 4-hydroxyphenyl-α-acetoxyacetic acid, 4-acetoxyphenyl-α-acetoxyacetic acid, 4-chlorophenyl-α-acetoxyacetic acid, 3-hydroxy-4-methoxyphenyl-α-acetoxyacetic acid, 4-hydroxy-3-methyl-α-acetoxyacetic acid, 3-(2-hydroxyphenyl)-α-acetoxypropanoic acid, 3-(4-hydroxyphenyl)-α-acetoxypropanoic acid, and 2-phenyl-β-acetoxypropanoic acid.

Additional useful α- or β-hydroxy acids and derivatives include aralkyl- and aryl-α-hydroxycarboxylic acids, polyhydroxycarboxylic acids, hydroxy-polycarboxylic acids, organicα-hydroxycarboxylic acids, α,α-hydroxycarboxylic acids, lactones, and cyclic esters of hydroxycarboxylic acids. Further examples of useful α- and β-hydroxy carboxylic acids and their derivatives may be found in U.S. Pat. Nos. 4,105,783, 4,518,789 and 5,258,391, which are incorporated herein by reference.

The chemical exfoliating agents are preferably used in combination with the polyester in a range of weight percentage ratios of from about 1:1 to about 20:1, more preferably from about 2:1 to about 10:1 chemical exfoliating agent to polyester. The range of weight percentage ratios can be adjusted based upon the degree of exfoliation desired. In addition, applicants have discovered that adjustments to the molecular weight of the polyester contribute to the ability to adjust the rate of desquamation for different strength formulations. For example, if a high rate of desquamation is desired for the chemical exfoliating formulation, than preferably, a lower molecular weight polyester having a molecular weight (MW) of from about 500 to about 1200 is used, more preferably about 700 to about 1000. As the molecular weight increases, the rate of desquamation can be controlled to a slower rate to allow cosmetic formulators to have control over the strength of the α-hydroxy formulation for different cosmetic uses, preferably, the molecular weights of polyesters for achieving a slower, but controlled rate of desquamation are from about 1200 to about 5000, more preferably from about 1200 to about 3000. In some cases, high rates of desquamation may contribute to an increase in irritation for some users, such that reducing the rate of desquamation will encourage the user to continue use which, over time, will enhance the cosmetic effect of the acid.

In addition to the ability to control the rate of desquamation, and regardless of monomeric branching or molecular weight, the use of the polyesters provides the additional benefit of reducing skin irritation of chemical exfoliating agents. The reduction in skin irritation provided by the polyesters is significant, because if the user of a formulation including the compositions of the present invention is advised to apply the formulation on a daily basis in order to achieve the desired effects, skin irritation will cause the user to interrupt usage or become dissatisfied with the formulation. Due to the reduced irritation and sensitization effect of the polyester, use on a regular basis can be achieved. Further, if the effects of reduced irritation and improved control or increased rates of desquamation are desired, the combined properties can be achieved by selecting a polyester having a molecular weight in the preferred molecular weight ranges as described above. By providing more control to the rate of desquamation and reducing skin irritation and sensitization, the long-term improvements to the users skin derived from the chemical exfoliating agents can be readily achieved.

The composition of polyesters and chemical exfoliating agents of the present invention may be used alone or in combination with any suitable cosmetic vehicle or base formulation which includes the composition. Additives which may be used include diluents, such as water, ethanol, glycerin and the like; preservatives such as methylparaben, propylparaben, sodium hydroxide solution and tetrasodium EDTA; emulsifiers and/or humectants such as triethanolamine, octyl stearate, glyceryl stearate, polyethylene glycol-100 stearate and propylene glycol; stabilizers such as 2,4-dichlorobenzyl alcohol, cetyl alcohol, aluminum starch octylsuccinate; emollients and/or emulsifiers such as isopropyl myristate, isopropyl palmitate, isopropyl stearate, cetearyl alcohol, cetyl-stearyl alcohol, ceteareth-20 and caprylic/capric triglyceride; stabilizers and/or thickeners such as hydroxyethylcellulose; acrylate polymers such as $C_{10\text{-}30}$ alkyl acrylate crosspolymer; suspension agents such as bentonite, sodium alginate, methyl cellulose and the like; surfactants such as sodium lauryl sulfate, dioctyl sodium sulfosuccinate, polyoxyethylene sorbitan monooleates; and sunscreens for UV protection such as p-amino benzoic acid (PABA) and PABA derivatives, octyl salicylate, homosalate, triethanolamine salicylate, 2-ethoxyethyl-p-methoxycinnamate; diethanolamine-p-methoxycinnamate, octyl methoxycinnamate, benzophenone-3 and other benzophenone derivatives, menthyl anthranilate; octocrylene; phenylbenzimidazole sulfonic acid, digalloyl trioleate, 3-(4-methyl benzylidene)camphor; 4-isopropyl dibenzoyl methane; 2-ethyl-2-cyano-3,3'-diphenyl acrylate and avobenzone. Other components, such as other inert ingredients, fragrances, stabilizers, emulsifiers, thickeners, humectants, colorants, further emollients, other film forming additives and preservatives, which will be known to those skilled in the art of cosmetic skin care formulations suitable for topical application may also be used.

In preparing topical formulations having a composition of the chemical exfoliating agents and polyesters according to the present invention, the formulations may be of a variety of types of base formulations in the form of a solid, a gel, a cream, an emulsion (water-in-oil or oil-in-water), an oil, an aerosol, an ointment, a solution, a sprayable and/or pumpable serun, or a lotion. Preferably, the formulations are creams, gels, emulsions, lotions, or oils suitable for applying to the skin. The limitations on the types of base formulations are dependent upon the particular chemical exfoliating agents and polyesters used in the composition such that when the composition is provided to the formulation, the composition is compatible and/or soluble with the other components in the formulation.

The chemical exfoliating agents are preferably provided to a topical formulation vehicle having a weight percentage in the range of from about 0.5 to about 50 weight percent of chemical exfoliating agent in an oil in water emulsion. For example, lactic acid can be provided in a sodium hydroxide buffered solution of lactic acid in water with a pH adjusted as desired. Typically the pH of the buffered solution is adjusted to between 3 and 5. The chemical exfoliating agents when provided to a cosmetic formulation are present in an effective amount for achieving desquamation and preferably are present in an amount of from about 0.5 to about 25 percent by weight, and more preferably from about 1 to about 10 percent by weight, of the entire formulation. Preferably, the polyesters are from about 0.5 to about 25 percent by weight and more preferably from about 1 to about 15 percent by weight of the entire formulation and are present within the range of ratios with respect to the chemical exfoliating agent as noted above. If there is not enough polyester, the enhancing effect caused by combination of the polyester and chemical exfoliating agent may not be sufficient.

The remaining additives, preservatives and the like provided to a formulation including the chemical exfoliating agents and polyesters and excluding the diluent may be added in an amount of up to about 35 percent by weight of the formulation with the remainder of the formulation being a diluent such as water, preferably deionized water. Depending on the type of formulation to be made, i.e., gel, emulsion, cream, and the like, there may be more or less of any of the above additional formulation components or varied types of additives, provided that the additives do not otherwise affect the beneficial effect achieved by combining the polyester(s) and chemical exfoliating agent(s).

The active ingredient used in combination with the polyesters according to the invention may also be a sunless tanning agent. Suitable sunless tanning agents are products which provide coloring to the user's skin without the need for exposure of the stratum corneum to harmful ultraviolet radiation. The agents react with amines in the stratum corneum, for example by a Maillard reaction, to yield colored (varied shades of brown) polymeric structures which link to the skin. The color of the structures is maintained on the surface of the skin generally for a few days. However, the polyesters of the present invention prolong this effect and maintain the structures on or in the stratum corneum for a longer period of time. Suitable examples of sunless tanning agents which may be used in accordance with the present invention include, without limitation, dihydroxyacetone, lawsone and juglone. Other suitable sunless tanning agents having similar properties to the sunless tanning agents mentioned herein are also within the scope of this invention.

The sunless tanning agents may be used alone in the composition with the polyesters or may be used in combination with other active ingredients such as insect repellents or chemical exfoliating agents. In addition, other typical skin care formulation additives such as those mentioned above with respect to the compositions including chemical exfoliating agents and polyesters according to the present invention. Preferably, the sunless tanning agents include sunscreens and/or chemical exfoliating agents to provide the beneficial anti-aging affects of the chemical exfoliating agents as well as to protect the stratum corneum from harmful UV radiation while allowing for a cosmetically achieved tan to develop. While such active ingredients and additives are not required in combination with the sunless tanning agents, most users of sunless tanning agents are interested in achieving a tan coloring without exposure to UV radiation and are similarly concerned with the aging effects of the sun such that the use of these active ingredients and additives in combination with the polyester would be advantageous.

The sunless tanning agents and polyesters are preferably used in a range of weight percentage ratios of from about 1:1 to about 50:0.1 more preferably from about 2:1 to about 10:1 sunless tanning agent to polyester. While the amount of polyester may be below this desired range, it may not sufficiently enhance the effect of the sunless tanning agents. Further, if there is an insufficient amount of sunless tanning agent, desired coloration may not be achieved. In the formulation, the amount of sunless tanning agent can be adjusted based upon the rate of coloration and the intensity of skin color desired. For example, in any sunless tanning agent formulation, increasing the weight percentage of the sunless tanning agent in the formulation generally increases the ability of the sunless tanning agent to achieve a darker tanning coloration level. However, the rate of tanning can be enhanced and controlled and the coloration prolonged by using the polyesters. Therefore, a desired and persistent level of color intensity is achieved sooner and can be retained for a longer period of time as a result of the polyesters. The polyesters, even with low amount of sunless tanning agent, fimction to hold the colored polymeric reaction product of the sunless tanning agents with the skin on or in the stratum corneum consistently and for prolonged periods allowing for improved color development and intensity.

Additives, such as those described above for use with compositions including chemical exfoliating agents and polyesters according to this invention may also be used in a formulation including sunless tanning agents and polyesters in amounts of up to 35 percent by weight, although this amount may be adjusted depending upon the type of base formulation desired. The sunless tanning agent compositions may be used in any of the types of base formulations suitable for topical application to the skin including, without limitation, creams, lotions, gels, emulsions, sprays and solids. The preferred base formulations are oil-in-water emulsions or creams. In a topically applied cosmetic formulation including the sunless tanning agent, the sunless tanning agent preferably comprises from about 2 to about 15 percent by weight and more preferably, from about 4 to about 10 percent by weight of the formulation. The polyester(s) are preferably provided in an amount of from about 1 to about 25 percent by weight and more preferably from about 4 to about 15 percent by weight of the formulation. As with formulations including the chemical exfoliating agents, the amount and type of additives provided will vary in accordance with the ultimate properties desired in the cosmetic formulation. In addition, any of the above-described polyesters may be used in combination with the sunless tanning agents. However, it will be understood by those of ordinary skill in the art, that it is preferred that additives and polyesters be selected which are compatible and soluble with each other in the formulation such that the formulation will be advantageously solubilized and resist separation and formulation inconsistency. In this regard, it is preferred that branched structure monomers, i.e., branched diols or diacids, be used in preparing the polyesters as the resulting backbone of the polyesters tend to be more compatible with typical topically applied skin care formulation additives.

Also within the scope of the present invention are combinations of the polyesters described above with skin lightening agents. Such additives are generally used in cosmetic formulations to make skin lighter. They are also used to reduce darker pigmentation effects on the skin such as freckles, blotches and other forms of hyperpigmentation. Many of these agents either retard or inhibit pigmentation or merely make the skin appear lighter cosmetically. Such products include formulations which merely apply pigmentation to the skin as well as those which reduce the rate of pigmentation of the skin or bleach the extracellular pigment. Cosmetic formulations which merely alter appearance must be applied daily. Those agents which slow the rate of pigmentation or which bleach the pigmentation are typically applied on definite intervals over a period of time. In either case, these agents function by removing color from melanin already in the skin and/or by preventing the formation of new melanin. The presence of polyesters in combination with such agents significantly and unexpectedly enhances their effect by holding the active agent on or in the stratum corneum for a longer period of time allowing them to achieve their goal by altering the pigmentation in the epidermal layer.

Suitable skin lightening agents for use in the present invention include the preferred skin lightening agents, hydroquinone and kojic acid. It will be understood, based on this disclosure, that other skin lightening agents providing similar skin lightening effects that would benefit from being substantially retained in or on the stratum corneum could be used within the scope of this invention.

The skin lightening agents and polyesters are preferably used in a range of weight percentage ratios of from about 1:1 to about 0. 1:20, and more preferably from about 1:2 to about 0.01:5 skin lightening agent to polyester. While the invention may be practiced outside these preferred ranges, if there is insufficient skin lightening agent in the composition, then the agent will not be able to effectuate the desired result. Further, if there is not sufficient polyester in relation to the skin lightening agent, then the polyester may not be able to sufficiently enhance the effects of the skin lightening agent.

The skin lightening agents may be used in any cosmetic or topically applied base formulations, including, without limitation, gels, lotions, creams, sprays, solvent-based solutions and cleansers, and solids. In addition, any suitable cosmetic additive may be provided to the base formulation provided it does not significantly effect the benefits of the present invention. Additives such as those mentioned above with respect to the compositions including the chemical exfoliating agents in combination with polyesters according to the present invention may also be used with the skin lightening agents. Such additives may be provided to a formulation including the skin lightening agent and polyester composition in amounts of up to about 35 percent by weight. Such amounts may vary, however, depending on the type of base formulation properties desired. Variations in the amount and type of additives used in preparing a desired base formulation for any of the embodiments according to the present invention using an active ingredient and polyester are within the abilities of those of ordinary skill in art.

Further, depending on the degree of intensity in skin lightening desired, it is preferred that the skin lightening agent be present in the base formulation in an amount of from about 0.1 to about 10 percent by weight, and more preferably, from about 0.1 to about 5 percent by weight of the formulation. The polyesters are preferably present in an amount of from about 0.5 to about 25 percent by weight, and more preferably from about 1 to about 10 percent by weight of the formulation. In addition, while any polyester will fall within the scope of the present invention, when forming a base formulation, it is preferred that a polyester be chosen which is readily compatible and soluble with the other selected components of the base formulation in order to avoid separation or poor consistency in the base formulation. Preferred polyesters for use in typical cosmetic topically applied formulations, such as lotions or creams, and which contribute to enhancing the effects of the skin lightening agents, include those polyesters which have a molecular weight of from about 500 to about 3,000, and more preferably from about 700 to about 1,000.

In addition to the additives noted above, the skin lightening agents may also be provided in combination with active ingredients such as the chemical exfoliating agents to provide the beneficial effects of the chemical exfoliating agents working with the polyesters according to the present invention as well as the benefits of the skin lightening agents. Sunscreens are also preferably provided as additives. Because the skin lightening agents are used to prevent or retard the formation of melanin, sunscreens can further assist in protecting the skin from otherwise harmful UV radiation, particularly if the skin lightening agents are used for topical applications intended for use by those who participate in outdoor activities.

In addition to chemical exfoliating agents, sunless tanning agents and skin lightening agents as active ingredients, applicants have also discovered that the polyesters described above provide an unexpectedly beneficial result when applied in conjunction with insect repellents. Insect repellents can be most effective if retained on or in the stratum corneum layers of the skin for prolonged periods of time in order to repel insects. Chemicals typically used as insect repellents may be detrimental if allowed to continuously be absorbed by the epidermis and to penetrate into the systemic circulation. Acute or chronic over-exposure of this nature can lead to severe neurological side effects. The skin can also become sensitized with allergic responses exacerbated by topical application of the insect repellent. To avoid such results, it is desired to find a cosmetic vehicle which keeps the insect repellent on the surface of the skin or in the outermost layers of the epidermis, without allowing it to penetrate to lower skin layers.

Such beneficial effects are achieved by the present invention. Insect repellents within the scope of this invention include alkyl monoethers of triethylene glycol, N,N-diethyl-m-toluamide (DEET), and other insect repellents which are most effective when applied topically and retained longer on or in the stratum corneum. Most preferably, the insect repellent is DEET. The insect repellent and polyester are preferably used in a composition according to the present invention in amounts in a range of weight percentage ratios of from about 0.25:1 to about 10:1, more preferably from about 1:1 to about 4:1 insect repellent to polyester. The insect repellent must be provided to any suitable composition or base formulation in an effective amount for providing insect repellency. The insect repellent and polyester may be provided to any suitable topical application base formulation, including, without limitation, gels, lotions, creams, solids and sprays.

When using the insect repellent in a base formulation including both the repellent and polyester, the insect repellent should be present in an effective amount, preferably from about 2 to about 75 percent by weight, and more preferably from about 5 to about 75 percent by weight of the total formulation. These amounts may vary depending on the selected type of topically applied base formulation.

While any polyester described above may be used in the present invention, preferably, the insect repellent and polyester are selected to be soluble and compatible with each other, and preferably, with other components in any base formulation, having preferred solubility parameters as discussed above. In addition, it is preferred that the molecular weight of the polyesters be from about 1,500 to about 20,000, and most preferably from about 2,000 to about 10,000. Exemplary preferred polyesters which are soluble up to 45 percent by weight in DEET include those with branched monomers and/or adipate-derived backbones, such as polyesters having backbones derived from neopentyl glycol adipate, trimethylpentane diol adipate, or diethylene glycol adipate and which have solubilities and molecular weights as discussed above. Also useful as a preferred polyester for DEET is glycerin/diethylene glycol/adipate cross-polymer which is commercially available as LEX-OREZ® 100 from Inolex Chemical Company of Philadelphia, Pa.

Additives typically used with insect repellent formulations intended for use in topically applied skin care formulations such as creams and lotions, may include any of the additives noted above with respect to the compositions having polyesters and chemical exfoliating agents according to the present invention. In addition, film forming agents in combination with suitable volatile solvents for applying the repellents in spray form may also be provided.

As outdoor activities become of increasing interest and insect-borne diseases of more concern, there is a need in the art for incorporation of insect repellents in desired outdoor skin care formulations which achieve insect repellency as well as other beneficial skin care effects. As such, it is preferred that additives such as sunscreens be provided for use with the insect repellent compositions according to the present invention. Further, it will also be desirable for users who apply cosmetic formulations including sunless tanning agents or skin lightening agents and/or chemical exfoliating agents on a regular basis to have an alternative outdoor formulation which will allow the user to apply only one such formulation when performing outdoor activities to avoid use of more than one skin care product application. The combination of these various active ingredients which applicants have discovered have enhanced results in combination with one or more polyesters will allow for substantially enhanced beneficial results in various combined topical compositions.

It should be understood from this disclosure that many various potential formulations can be made by incorporating one or more active ingredients in combination with one or more polyester as described herein thereby providing the cosmetic formulator with many possibilities for improved cosmetics or topically applied compositions achieving the beneficial results as described herein without departing from the scope of this invention. The polyesters achieve an enhanced performance with respect to certain active ingredients which benefit from the ability of the polyesters to substantially retain the active ingredients on or within the stratum corneum for prolonged periods of time without penetrating lower layers of the skin.

The present invention also includes a method for improving the effect of an active ingredient in a topical composition. The method includes providing one or more polyester, such as those polyesters described above with respect to the compositions of the present invention, to a topical composition. The active ingredients preferably used within the scope of the method of the present invention include one or more of a chemical exfoliating agent, sunless tanning agent, skin lightening agent, and insect repellent such as those described above. The active ingredients and polyesters may be added in amounts and combined in ratios such as those described herein. The method may also include addition of any suitable preferred additives for preparing base formulations including the active ingredients and polyesters as described above. The polyesters according to the present method function to substantially retain the active ingredient on or in the stratum corneum thereby improving the desired effect of the active ingredient. The order and type of phases used for combining the various additional formulation components including the compositions of the present invention may vary in accordance with the desired end formulation and is within the capabilities of those of ordinary skill in the art. Examples of typical cosmetic formulations are included below.

The invention will now be described in more detail with respect to the following, non-limiting examples:

EXAMPLE 1

The process of desquamation of the skin involves the movement of basal cells of the viable epidermis to the outermost layers of the epidermis. With an accelerated exfoliation rate, the cells in the basal layer differentiate and migrate to the outermost layers of the epidermis more rapidly, resulting in a faster cell renewal and turnover rate. As such, the length of time during which the basal cells can differentiate is decreased. As the rate of cell renewal is increased, epidermal squamous cells become smaller in diameter than they would be during periods of less rapid cell renewal. In order to measure the effect of the rate of cell turnover, we examined the size of cells taken from the outermost epidermal skin layer.

Lotions with a pH of 3.4 to 3.6 having 10 percent active undissociated lactic acid were applied to the forearms of subjects daily for a period of one month. Cells were removed weekly and their size measured. The lotions were all identical with the exception of the delivery aid used. The comparative results demonstrate the relative effect of the varying delivery aids. Polyesters having a trimethylpentane (TMPD) diol adipate backbone and having a low molecular weight produced the greatest, most sustained decrease in cell size. The test composition is shown below in Table 1:

TABLE 1

| | Hydroxy Acid Composition Components | Weight Percentage (%) |
|---|---|---|
| A | Deionized Water | qs to 100% |
| | 2,4-Dichlorobenzyl alcohol | 0.16 |
| B | Cetearyl alcohol and Ceteareth-20 | 3.50 |
| | Cetyl-Stearyl Alcohol | 2.00 |
| | Caprylic/Capric Triglycerides Delivery Aid | 5.00 |
| C | Buffered Sodium Lactate Solution | qs to 10% active undissociated lactic acid, final pH 3.4–3.6 |

The 2,4-dichlorobenzyl alcohol, cetearyl alcohol, ceteareth-20, and caprylic/capric triglycerides were from Inolex Chemical Company. The cetyl-stearyl alcohol was obtained from Rhone-Poulenc. Part C of the above test composition was an oil-in-water emulsion with 10 percent lactic acid buffered with sodium hydroxide. The Delivery Aids used in the experimental compositions are listed below in Table 2.

TABLE 2

| Sample Number | Delivery Aid |
|---|---|
| 1 | Poly (TMPD adipate) isononanoate, MW = 800 |
| 2 | Poly (TMPD adipate) diol, MW = 800 |
| 3 | Poly (TMPD glycerol adipate) polyol, MW = 800 |
| 4 | Poly (TMPD adipate) diol, MW = 1500 |
| 5 | Poly (TMPD glycerol adipate) polyol, MW = 1500 |
| 6 | Propylene Glycol |

TABLE 2-continued

| Sample Number | Delivery Aid |
|---|---|
| 7 | Control Formula-No Delivery Aid |
| 8 | Control Formula-No Delivery Aid and No Buffered Lactic Acid |

The control compositions (Samples 7 and 8) both included no delivery one of the control compositions (Sample No. 8) also contained no buffered lactic acid.

To test the compositions, 18 subjects were tested. Each was tested with two of the compositions. The application site was an area of 5 cm×15 cm on the volar forearm. One of the assigned example compositions was applied to one site and the other to the another equivalent site on the other arm. The subjects then applied 0.3 cm$^3$ of each lotion using a 1 cm$^3$ Insulin syringe from Bectin Dickinson to allow for consistent application volume. The lotions were applied twice daily, once in the morning and once in the evening with at least 6 hours between applications. The dosage schedule was reduced to once daily applications of 0.3 cm$^3$ on day 16, and continued to the end of the study on day 27. Skin samples were removed on days 0, 7, 14, 21, and 28. The presence of lotion on the application site affected photomicrograph quality, so the morning application was eliminated on sampling days.

Skin sampling was performed by retrieving surface biopsies on days 0, 7, 14, 21, and 28 from each application site. The arms of the subjects were wetted for 5 seconds with a gauze pad saturated in deionized water. The sites were allowed to air dry until no water was visible upon observation. D-Squame Skin Surface Sampling Discs, available from CuDerm Corporation, 12.7 mm in diameter were placed on the skin using forceps and pressure was applied to the D-Squame in an amount of less than about 0.912 N·cm$^{-2}$. The D-Squames were removed from the skin with forceps.

The D-Squames were stained with Chlorazol Black E Fungal Stain, available from Delasco Dermatologic Lab & Supply, by placing the D-Squame, adhesive side up, on a clean glass microscope slide. Stain was dropped onto the adhesive surface until most of the disc was covered by a large drop of stain. The stain was left in place for 11 minutes. The D-Squame was then rinsed by submersing in fresh deionized water. The D-Squame was placed, adhesive side down, onto a clean glass microscope slide for observation using an Olympus Polarizing Microscope Model BHSP with a PM-10-35ASD-2 Automatic Photomicrographic System. Photomicrographs were recorded on Kodak Plus-X pan film at 152× magnification. The film was then developed using Kodak Microdol-X developer.

The negatives were projected onto a flat white surface at 11.5× enlarger magnification using an Omega C-700 Enlarger set to an F-stop of 3.5. The individual cells were measured in two dimensions, treating each cell as a square as much as possible. The two dimensions were recorded and used to calculate cell areas. Two negatives per site per sampling day were projected for cell measurement. Special attention was taken to account for cells overlapping each other.

Because different people have cells of different size it was necessary to develop a baseline treatment. The average cell size on day 0 for each site served as the baseline measurement. Average cell sizes for each site for subsequent sampling days were compared to day 0 to determine the amount of change in percent difference between the sampling day and day 0. The average percentage change in cell size from day 0 for each sampling day for each Sample composition is found below in Table 3.

TABLE 3

| Sample Number | Day 7 % Change | Day 14 % Change | Day 21 % Change | Day 28 % Change |
|---|---|---|---|---|
| 1 | −5.3 | −8 | −5.3 | 2.2 |
| 2 | −6.5 | −11.2 | −7.6 | −4 |
| 3 | −8.18 | −5.98 | N/A | −2.11 |
| 4 | −3.42 | 5.31 | 6.09 | −0.3 |
| 5 | 2.58 | 4.74 | 16.06 | 5.74 |
| 6 | −4.2 | −10.8 | 0.10 | 7.5 |
| 7 | −0.81 | −2.87 | −3.48 | −1.68 |
| 8 | 0.6 | −0.10 | −1.7 | −1.4 |

As noted above in Table 3, in all cases change in cell size was observed. Cells removed from subjects having control Sample No. 8, which contained no lactic acid delivery aid, displayed the smallest amount of change in cell size. In subjects applying the other control, Sample No. 7, having no polyester, but containing 10 percent undissociated lactic acid, the average percentage change in cell size was more pronounced than that of control Sample No. 8. The subjects who applied the lotion which contained propylene glycol (Sample No. 6), generally regarded in the personal care industry as a penetration enhancer, exhibited a more pronounced decrease in cell size early in the study than the subjects using only acid (Sample No. 7), but that change did not persist over the course of the study. The change in cell size exhibited by subjects who applied the lotions with the polyester polymers was not consistently negative. The lotions containing the lower molecular weight polyester polymers (Samples Nos. 1, 2 and 3) caused a decrease in cell size which persisted for the length of the study. In contrast, the lotions containing the higher molecular weight polyester polymers (Samples 4 and 5) caused an increase in cell size rather than a decrease. The increased cell size is due to less cell turnover. The faster the cells move from the basal layer to the upper epidermis, as with increased rates of exfoliation, the less time they have to differentiate, resulting in smaller cell size.

Subjects applying the lower molecular weight polyesters displayed the most negative response in cell size. When compared to the control formulas (Samples 7 and 8), the effects of applying the alpha hydroxy acid lotion are of greater magnitude and are more prolonged even when the dosage was reduced 50 percent (Day 16). The Sample with propylene glycol (Sample No. 6) also exhibited a pronounced negative change in cell size. However, following the reduction in dosage, the effects of the alpha-hydroxy acid lotion were not sustained as with the lower molecular weight polyesters.

The decrease in cell size is evidence of an accelerated rate of exfoliation and cell turnover. As molecular weight decreases, an increase in desquamation occurs. Lower molecular weight polyesters tend to enhance the exfoliation performance of the hydroxy acids, as well as not compromising the effects of the acid with reduced dosage of product. As such, it is preferred that polyesters be selected in accordance with the preferred molecular weights as noted above.

By using a low molecular weight polyester, the composition of an alpha-hydroxy acid product will contribute to a sustained skin response. As a result, a beneficial effect can be achieved from the alpha-hydroxy acid by using less in an applied composition or using the composition in smaller applied amounts. With the polyesters' ability to sustain the effects of the acid, missing a day, or reducing the amount will not have a deleterious effect on the perceived performance of the lotion. The ability to reduce the dosage without seriously compromising an alpha-hydroxy acid product's performance can be very important when a user is especially sensitive to the acid in the product.

EXAMPLE 2

Three polyesters were examined for their effect on dihydroxyacetone-containing sunless tanning products. The experiment examined what the effects with respect to color formation and color persistence, when different polyesters were provided to a base composition. Four compositions were used overall. The control composition contained no polyester. Table 4 below provides the base composition.

TABLE 4

| Composition Phase | Composition Component | Weight Percentage (%) |
| --- | --- | --- |
| Aqueous Phase | Deionized Water | 60.80 |
| | 2,4-Dichlorobenzyl Alcohol | 0.20 |
| | Propylene Glycol | 1.00 |
| Oil Phase | Cetearyl Alcohol and Ceteareth-20 | 5.00 |
| | Ethylhexyl-p-methoxycinnamate | 6.00 |
| | Benzophenone-3 | 3.00 |
| | Polyester | 5.00 |
| DHA Solution | Dihydroxyacetone | 4.00 |
| | Deionized Water | 15.00 |
| | Citric Acid | qs to pH 3.5 to 4.0 |

While not necessary to the compositions, sunscreens were added to the base formulation to allow skin coloration to occur without damaging UV radiation. The compositions used had the following components listed in Table 5 below substituted as the Polyester in Table 4 above. The control (Sample No. 9) contained 5.00 percent additional deionized water instead of a polyester.

TABLE 5

| Sample No. | Substituted As Polyester Component in Composition |
| --- | --- |
| 9/9A | Deionized Water Substituted for Polyester (Control) |
| 10/10A | Poly (diethylene glycol glycerol adipate) polyol, MW = 3000 |
| 11/11A | Poly (neopentyl glycol glycerol adipate) polyol, MW = 3000 |
| 12/12A | Poly (neopentyl glycol adipate) diol, MW = 7500 |

To apply compositions, two areas of the subjects's right thigh were designated. Within each area, four 2.54 cm×2.54 cm areas were marked using an ink pen. Each formula was applied to one square in each area so that there would be two applications of each composition. In one area, 0.05 g of each composition was applied for samples Nos. 9–12. In the other area, 0.09 g of each composition was applied for samples Nos. 9A–12A. This was done to ensure that different amounts of applied DHA-containing composition would not produce the same degree of skin color. Once the compositions were applied, special care was taken to ensure that the application areas would not be disturbed until after the three hour evaluation was made. Evaluations of color were made at three hours, and then daily from day 1 to day 15. No reporting was available for days 2, 5, 8 and 0. The sites were scored on a scale from 0 to 4, with a score of 0 indicating a lack of color on the application site. A score of 4 indicated that the color was very dark. Initially, no provision for fractional scores was made, but the persistence of very slight skin coloration at the end of the study necessitated the adoption of scores less than 1 and greater than 0. The results are shown below in Table 6.

TABLE 6

| | Sample Number/Area 1 (0.05 g) | | | | Sample Number/Area 2 (0.09 g) | | | |
| --- | --- | --- | --- | --- | --- | --- | --- | --- |
| Test Day | 9 | 10 | 11 | 12 | 9A | 10A | 11A | 12A |
| 3 hours | 2 | 1 | 1 | 0 | 2 | 1 | 2 | 1 |
| 1 | 4 | 3 | 4 | 3 | 4 | 3 | 4 | 4 |
| 3 | 3 | 4 | 4 | 3 | 4 | 4 | 4 | 4 |
| 4 | 3 | 3 | 3 | 3 | 3 | 4 | 4 | 4 |
| 6 | 2 | 2 | 3 | 2 | 3 | 4 | 4 | 4 |
| 7 | 2 | 2 | 2 | 2 | 2 | 3 | 4 | 4 |
| 10 | 1 | 2 | 2 | 2 | 2 | 3 | 3 | 3 |
| 11 | 1 | 1 | 1 | 1 | 1 | 2 | 1 | 2 |
| 12 | 0 | 0.5 | 1 | 1 | 1 | 1 | 1 | 2 |
| 13 | 0 | 0 | 0.5 | 0.5 | 0.5 | 1 | 0.5 | 1 |
| 14 | 0 | 0 | 0 | 0 | 0 | 0.5 | 0.5 | 0.5 |
| 15 | 0 | 0 | 0 | 0 | 0 | 0 | 0 | 0.5 |

Although observations at three hours indicated that little skin coloration had developed, on day 1, all sites had developed significant skin coloration. The areas with the greater weight of composition applied exhibited slightly darker skin coloration and persistence of skin color, see, e.g., the end point day 15 in comparison with day 13 for the Area 1 sites. The formulas with the polyesters did not consistently out perform the control composition in terms of color development. However, the compositions with the polyesters consistently outperformed the control formula in terms of persistence of color. The control compositions had endpoints of 11 days for 0.05 g applied and 13 for the days for 0.09 g applied. The application sites for the polyester compositions exhibited skin coloration longer when compared against the corresponding control at the same applied weight composition. The results indicate that by including polyesters in a composition, color can be maintained with less total DHA applied. The end point for the two neopentyl-based polyester compositions applied with weights of 0.05 g was 13 days which is the same as the site where 0.09 g of the control composition was applied. The addition of polyesters to DHA-based sunless tanning products allows for the development of persistent, intense color using less DHA, a situation that aids both the manufacturer and the consumer.

EXAMPLE 3

The formulation of new melanin in the basal layers of the skin may be inhibited by the application of suitable agents with the result that the newly generated epidermis has a lower pigment content and is therefore lighter in color. By incorporating polyester into compositions containing these agents, the agents have a chance to work more effectively in the epidermis of the skin. Two compositions were prepared, both of which exhibited excellent results in enhancing the lightening effects of the skin lighteners, hydroquinone and kojic acid. While not necessary, sunscreens were also provided to the compositions to reduce the effects of ultraviolet radiation which may contribute to irregular pigmentation. The sunscreens used were 6 percent octyl methoxycinnamate and 3 percent benzophenone-3. The compositions are shown below in Table 7 and 8.

TABLE 7

| Composition Component | Weight Percentage (%) |
|---|---|
| Deionized Water | qs to 100 |
| Propylene Glycol | 5.00 |
| Hydroquinone | 2.00 |
| Sodium Metabisulfate | 0.05 |
| Ascorbic Acid | 0.05 |
| Glyceryl Stearate (and) Sodium Lauryl Sulfate | 15.00 |
| Glyceryl Stearate | 6.00 |
| Stearyl Alcohol | 3.00 |
| Propylparaben | 0.10 |
| Poly(trimethylpentane diol adipate) diol, MW = 1,500 | 5.00 |
| Octyl Methoxycinnamate | 6.00 |
| Benzophenone-3 | 3.00 |

TABLE 8

| Composition Component | Weight Percentage (%) |
|---|---|
| Deionized Water | qs to 100 |
| Propylene Glycol | 5.00 |
| Kojic Acid | 1.00 |
| Stearic Acid | 5.00 |
| Cetearyl Alcohol | 1.00 |
| Octyl Stearate | 4.00 |
| Glyceryl Stearate | 3.00 |
| Triethanolamine | 0.50 |
| Poly(neopentyl glycol glycerol adipate) polyol, MW = 3,000 | 5.00 |
| Octyl methoxycinnamate | 6.00 |
| Benzophenone-3 | 3.00 |

EXAMPLE 4

The ability of a polyester polyol to mitigate the penetration of human skin by sunscreen actives is disclosed in co-pending U.S. patent application Ser. No. 08/673,707, incorporated herein by reference. In experiments measuring the recovery of sunscreen actives octyl methoxycinnamate and benzophenone-3, the amount of both actives recovered from the skin and outer stratum corneum increased when the polyester, LEXOREZ® 100, available from Inolex Chemical Company, was added to a solution of the actives. Solubility studies by the applicants have found that polyester polyols and diols with trimethylpentane adipate diol, neopentyl glycol adipate, and diethylene glycol adipate backbones are soluble in N,N-diethyl-m-toluamide (DEET) up to 45 percent by weight.

Studies were also conducted to determine if recovery of DEET applied to human skin would be increased by the addition of a polyester polyol. Experimental preparations as shown below in Table 9.

TABLE 9

| Composition Component | Weight Percentage (%) Control | Weight Percentage (%) Experimental |
|---|---|---|
| N,N-dimethyl-m-toluamide | 100.00 | 75.00 |
| LEXOREZ® 100 | 0.00 | 25.00 |

On a subject's volar forearm, three non-overlapping, 5.08 cm×7.62 cm rectangular sites were marked using a Water Resistant Lab Marker, from Baxter. A 2 cm×4 cm rectangle was drawn in the center of each 5.08 cm×7.62 cm rectangle using the same Lab Marker. The smaller rectangles were the actual application sites. Locating them inside the larger rectangles prevented samples from interfering with each other and allowed for greater consistency in tape stripping. The sites were pre-stripped three times each by applying tape (Scotch Brand Premium Heavy-duty Box Sealing Tape #3750, Clear, from 3M Corporation) to the skin, pressing on the tape, and pulling the tape off of the skin. The solutions were applied to the application area using wooden applicator sticks (5.25 in long with 0.085 in diameter from Fisher Scientific Co.) The average weight applied was 6.17 mg for the control composition and 9.47 mg for the experimental composition. After a residence time of 1 hour, each site was tape stripped 5 times. To avoid contamination, latex rubber gloves were worn (Perry X-Am Style 312).

After each application site was stripped and each tape strip was placed individually into a separate 20 mm×150 mm test tube with screw-on cap, 15 ml of tetrahydrofuran (THF) (HPLC Grade, Fisher Scientific Co.) was added to each test tube using a 15 ml glass volumetric pipette. The test tube openings were covered with a small piece of aluminum foil, and the tubes were capped and shaken. The test tubes with the tape strips in THF sat for at least 45 minutes or until the adhesive was visibly dissolved off of the tape. Samples from each test tube were transferred to gas chromatography (GC) vials for analysis using a Perkin Elmer Autosystem Gas Chromatograph with Flame Ionization Detector, megabore capillary column (30 m×0.53 mm inner diameter and 1.5 micron film thickness) Model DB-5 from J. And W. Scientific. A Perkin Elmer Nelson Turbochrom Navigator v.4.1 PC interface was used. DEET peak areas produced by the samples were correlated by retention time and quantified by comparing against prepared standard solutions of known concentrations. The total amount of DEET recovered per application site was determined by adding the amount recovered from tape strips 1–5 for each site. Dividing the total amount recovered by the total amount applied for each site provided the percentage recovery for each application site. The average percentage recovery of DEET for the control and experimental solutions are listed in Table 10.

TABLE 10

| Solution | Average Percentage Recovery of DEET (%) |
|---|---|
| Experimental (with 25% LEXOREZ® 100) | 83.25% |
| Control | 79.17% |

The goal of this study was to determine the ability of LEXOREZ® 100 to mitigate skin penetration by DEET. When LEXOREZ® 100 was included in combination with DEET, the average percentage recovery of DEET was greater than that measured for a solution with no polyester. As such, polyesters, such as LEXOREZ® 100 mitigate skin penetration of DEET.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A topical composition for application to the stratum corneum, comprising:
   (a) a polyester; and
   (b) an effective amount of an active ingredient selected from the group consisting of a sunless tanning agent present in a weight percentage ratio of from about 1:1 to about 50:0.1 of the sunless tanning agent to the polyester, and a skin lightening agent present in a weight percentage ratio of from about 1:1 to about 0.1:20 of the skin lightening agent to the polyester, wherein the polyester functions to substantially retain the active ingredient on or in the stratum corneum.

2. The composition according to claim 1, wherein the polyester has a Hildebrand solubility parameter of from about 5 to about 25 and a molecular weight of from about 500 to about 100,000.

3. The composition according to claim 1, wherein the polyester has a backbone derived from the reaction of at least one linear or branched diol and at least one linear or branched diacid, said backbone being acid or hydroxy functionalized, and said polyester having a molecular weight of from about 500 to about 100,000.

4. The composition according to claim 3, wherein said at least one diacid comprises from 2 to 10 ether linkages.

5. The composition according to claim 3, wherein said at least one diacid comprises from 2 to 10 tertiary amine groups.

6. The composition according to claim 3, wherein said at least one diol and said at least one diacid each have from 2 to 20 carbon atoms.

7. The composition according to claim 3, wherein said backbone is further the reaction product of at least one polyfunctional alcohol having a functionality of at least 3 or at least one polyfunctional acid having a functionality of at least 3 and said polyfunctional alcohol or polyfunctional acid is present in an amount of up to 50 percent by weight of all reactants.

8. The composition according to claim 3, wherein said backbone is derivatized by a reaction of end groups of said polyester backbone and a compound selected from the group consisting of linear and branched, saturated and unsaturated aliphatic monofunctional acids of from 2 to 40 carbon atoms, linear and branched saturated and unsaturated aliphatic monofunctional alcohols of from 2 to 40 carbon atoms, primary amines, secondary amines, and silicon-containing compounds.

9. A topical composition for application to the stratum corneum, comprising:
  (a) a polyester having a backbone derived from the reaction of at least one linear or branched diol and at least one linear or branched diacid, and said polyester having a molecular weight of from about 500 to about 100,000; and
  (b) an effective amount of an active ingredient selected from the group consisting of a sunless tanning agent present in a weight percentage ratio of from about 1:1 to about 50:0.1 of the sunless tanning agent to the polyester, and a skin lightening agent present in a weight percentage ratio of from about 1:1 to about 0.1:20 of the skin lightening agent to the polyester, wherein the polyester functions to substantially retain the active ingredient on or in the stratum corneum.

10. A method for improving an effect of an active ingredient in a topical composition, comprising providing to said topical composition a polyester in an amount effective for enhancing the effect of the active ingredient, wherein said active ingredient is selected from the group consisting of a sunless tanning agent present in a weight percentage ratio of from about 1:1 to about 50:0.1 of the sunless tanning agent to the polyester, and a skin lightening agent present in a weight percentage ratio of from about 1:1 to about 0.1:20 of the skin lightening agent to the polyester, and said polyester functions to substantially retain the active ingredient on or in the stratum corneum to improve an effect of said active ingredient, and the polyester is co-soluble with the active ingredient.

11. A topical composition for application to the stratum corneum, comprising:
  (a) a polyester, and
  (b) an effective amount of an insect repellent, wherein the polyester functions to substantially retain the insect repellent on the stratum corneum and the insect repellent is present in a weight percentage ratio of the insect repellent to the polyester of from about 0.25:1 to about 10:1.

12. A method for improving an effect of an insect repellent in a topical composition, comprising providing to said topical composition a polyester, wherein the polyester functions to substantially retain the insect repellent on the stratum corneum and minimize penetration of the insect repellent into the stratum corneum, the insect repellent is present in an amount effective to provide insect repellency and the insect repellent is present in a weight percentage ratio of the insect repellent to the polyester of from about 0.025:1 to about 10:1.

13. A topical composition for application to the stratum corneum, comprising:
  (a) a polyester having a backbone derived from the reaction of at least one linear or branched diol and at least one linear or branched diacid, said backbone being acid or hydroxy functionalized, and the polyester having terminal groups selected from the group consisting of —OH, —(C=O)OH, —O(C=O)R', and —(C=O)OR', wherein R' is independently a linear or branched hydroxy-substituted or unsubstituted aliphatic $C_2$–$C_{60}$ group with from 0 to 200 ether linkages, a hydroxy-substituted or unsubstituted cyclic aliphatic $C_2$–$C_{12}$ group, or a hydroxy-substituted or unsubstituted aromatic group; and
  (b) an effective amount of a chemical exfoliating agent, wherein the polyester functions to substantially retain the chemical exfoliating agent on or in the stratum corneum and the chemical exfoliating agent is present in a weight percentage ratio of the chemical exfoliating agent to the polyester of from about 1:1 to about 20:1.

14. The composition according to claim 13, wherein said backbone is derivatized by a reaction of the terminal groups of said polyester backbone with a silicon-containing compound.

15. A method for improving an effect of a chemical exfoliating agent in a topical composition, comprising providing to said topical composition a polyester wherein the polyester functions to substantially retain the chemical exfoliating agent on or in the stratum corneum, the chemical exfoliating agent is present in an amount effective to cause desquamation and in a weight percentage ratio of the chemical exfoliating agent to the polyester of from about 1:1 to about 20:1 and the polyester has a backbone derived from the reaction of at least one linear or branched diol and at least one linear or branched diacid, said backbone being acid or hydroxy functionalized, and the polyester having terminal groups selected from the group consisting of —OH, —(C=O)OH, —O(C=O)R', and —(C=O)OR', wherein R' is independently a linear or branched hydroxy-substituted or unsubstituted aliphatic $C_2$ $C_{60}$ group with from 0 to 200 ether linkages, a hydroxy-substituted or unsubstituted cyclic aliphatic $C_2$–$C_{12}$ group, or a hydroxy-substituted or unsubstituted aromatic group.

16. The composition according to claim 12, wherein said polyester minimizes skin irritancy resulting from said chemical exfoliating agent when said composition is topically applied to a surface of the stratum corneum.

17. The composition according to claim 16, wherein said polyester also improves the rate of desquamation of said composition when topically applied to a surface of a stratum corneum.

18. The composition according to claim 17, wherein said polyester has a molecular weight from about 500 to about 5,000.

19. The composition according to claim 16, wherein said polyester has a backbone derived from trimethylpentane diol adipate.

20. The composition according to claim 16, wherein said polyester is cross-linked with glycerol.

21. The composition according to claim 16, wherein said chemical exfoliating agent is selected from the group consisting of alpha-hydroxy acids, beta-hydroxy acids, and proteolytic enzymes.

22. The composition according to claim 1, wherein said active ingredient is a sunless tanning agent, and said polyester improves the persistence of color development when said composition is topically applied to a surface of a stratum corneum.

23. The composition according to claim 22, wherein said sunless tanning agent is selected from the group consisting of dihydroxyacetone, lawsone, and juglone.

24. The composition according to claim 22, wherein said polyester has a backbone derived from the reaction of at least one branched diol and at least one branched diacid, said backbone having acid or hydroxy functionality.

25. The composition according to claim 22, wherein said polyester has a backbone selected from the group consisting of diethylene glycol adipate, and neopentyl glycol adipate.

26. The composition according to claim 22, wherein said polyester is cross-linked with glycerol.

27. The composition according to claim 1, wherein said active ingredient is a skin lightening agent, and said polyester minimizes the rate of formation of melanin in basal layers of skin when said composition is topically applied to a stratum corneum.

28. The composition according to claim 27, wherein said skin lightening agent is selected from the group consisting of kojic acid, and hydroquinone.

29. The composition according to claim 27, wherein the polyester has a molecular weight of from about 500 to about 3,000.

30. The composition according to claim 11, wherein said insect repellent is N,N-diethyl-m-toluamide.

31. The composition according to claim 30, wherein said polyester has a backbone which is a reaction product of at least one diol, at least one diacid and at least one polyfunctional alcohol or polyfunctional acid present in an amount up to 50 percent by weight and the molecular weight of said polyester is from about 1,500 to about 20,000.

32. The composition according to claim 31, wherein said polyester is cross-linked with a glycerol.

\* \* \* \* \*